United States Patent [19]
Yamamoto et al.

[11] Patent Number: 5,273,841
[45] Date of Patent: Dec. 28, 1993

[54] SULFURIC ACID CONCENTRATION SENSOR AND LEAD ACID BATTERY EQUIPPED WITH SULFURIC ACID CONCENTRATION SENSOR

[75] Inventors: Takakazu Yamamoto, 26-18, Edaminami 4-chome, Midori-ku, Yokohama-shi, Kanagawa, Japan; Shigeru Sano, Takatsuki, Japan

[73] Assignees: Yuasa Battery Co., Ltd., Takatsuki; Takakazu Yamamoto, Yokohama, both of Japan

[21] Appl. No.: 904,324

[22] Filed: Jun. 25, 1992

[30] Foreign Application Priority Data

Jul. 1, 1991 [JP] Japan .................... 3-160429
Jun. 5, 1992 [JP] Japan .................... 4-145447

[51] Int. Cl.⁵ .................... H01M 10/48; G01N 27/02
[52] U.S. Cl. .................... 429/92; 324/439
[58] Field of Search .................... 429/92; 324/439, 446

[56] References Cited

U.S. PATENT DOCUMENTS

| | | | |
|---|---|---|---|
| 2,000,668 | 5/1935 | Pease | 324/446 X |
| 3,173,969 | 3/1965 | Kapff | 324/439 X |
| 4,320,291 | 3/1982 | Uramoto | 429/92 X |
| 4,913,987 | 3/1990 | Datillo | 429/92 |

FOREIGN PATENT DOCUMENTS

| | | | |
|---|---|---|---|
| 55-163781 | 12/1980 | Japan | 429/92 |
| 60-68551 | 4/1985 | Japan | |
| 3-075552 | 3/1991 | Japan | 324/446 |

*Primary Examiner*—Stephen Kalafut
*Attorney, Agent, or Firm*—Armstrong, Westerman, Hattori, McLeland & Naughton

[57] ABSTRACT

A sulfuric acid concentration sensor including a sensor body comprising a high molecular compound having a property to react with sulfuric acid and a property to change an electric conductivity in such a way as one-valued function with a change in sulfuric acid concentration, in which an electric current is flown through the sensor body impregnated in sulfuric acid solution to obtain the electric conductivity of sensor body so as to know the sulfuric acid concentration. Since the electric conductivity of high molecular compound changes corresponding to the sulfuric acid concentration, the sulfuric acid concentration can be known when the electric conductivity of the sensor body i.e. the high molecular compound is obtained, so that the concentration of sulfuric acid can be measured easily.

11 Claims, 3 Drawing Sheets

SULFURIC ACID CONCENTRATION SENSOR AND LEAD ACID BATTERY EQUIPPED WITH SULFURIC ACID CONCENTRATION SENSOR

BACKGROUND OF THE INVENTION

1. Field of the Invention

This invention relates to a sulfuric acid concentration sensor enabling an easy measurement of the concentration of sulfuric acid and a lead acid battery equipped with such a sulfuric acid concentration sensor.

2. Description of the Prior Art

Sulfuric acid is used widely in industrial fields, and it is frequently required to know the concentration of sulfuric acid when using it. Accordingly, a measurement of the concentration of sulfuric acid is very significant matter from the industrial viewpoint. In a lead acid battery for example, its sulfuric acid concentration varies according to charging and discharging as expressed by the following equation (II), so that a charge/discharge quantity of a lead acid battery can be measured by measuring the sulfuric acid concentration. If the sulfuric acid concentration can be measured easily, the charge/discharge quantity of the lead acid battery can be controlled. Since the sulfuric acid concentration normally varies within a range of 8 to 45% in the charging and discharging of lead acid battery, it is generally said that the measurement in this range of concentration is specially important.

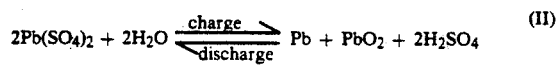

$$2Pb(SO_4)_2 + 2H_2O \xrightleftharpoons[\text{discharge}]{\text{charge}} Pb + PbO_2 + 2H_2SO_4 \quad (II)$$

The large portion of lead acid batteries are used for starting automobiles. However, when the battery is in an insufficiently charged state, its residual capacity is not enough to carry out the starting operation. Since a driver has not been able to previously know such a defective state, he has encountered much troubles so far. If the charged state can be known in advance, countermeasures can be taken such as carrying out a supplementary charging before stopping the automobile. Therefore, there has been a strong demand for a lead acid battery equipped with a sensor capable of indicating a charge/discharge quantity. In existing generators, a charging current at the time of charge end is controlled by a charging voltage, however, a control suitable for the battery can not be executed because the charge voltage changes according to a temperature and history of battery etc. On the contrary, the specific gravity of the electrolyte, i.e., the sulfuric acid concentration, correctly indicates the charge/discharge quantity. Consequently, the charge end can be known exactly by the sulfuric acid concentration so that a charge control suitable for the battery can be executed. For this reason, there has been a strong demand for a lead acid battery equipped with a sensor capable of indicating a charge/discharge quantity on the basis of the sulfuric acid concentration.

As methods for measuring the sulfuric acid concentration, those shown by the following (1) to (4) have been known so far. They each include respective problems and are expensive in manufacturing cost, so that they have not been put in practical use for a sulfuric acid concentration sensor of lead acid battery for automobile.

(1) Refractive index measurement method

This is a measurement method utilizing a property of the sulfuric acid that its refractive index changes according to its concentration, and a measurement device is composed of a light emitting diode, a light receiving diode and an optical path. This method requires a comparatively long optical path in a sulfuric acid solution which is an object of measurement, and conversion of light into an electrical current, so that a compact and inexpensive sensor can not be fabricated. Although this sensor is now used in a stationary lead acid battery, it has not so far been put to practical use for an automobile lead acid battery.

(2) Specific gravity measurement method

This is the method for measuring a specific gravity of sulfuric acid utilizing a float, which is inexpensive and convenient, but is difficult in accomplishing an automatic reading. Further, this method includes various difficulties from the standpoints of manufacturing cost and structure in order to take in the specific gravity as an electrical signal into a control system.

(3) Electrochemical method

This is a measurement method in which a sensor electrode system comprising a metal, sulfuric acid and metal oxide is prepared separately, so as to measure the concentration by means of its dependency of electromotive force on the sulfuric acid concentration. An appropriate electrode system has not not found as of yet, and the existing system has the disadvantage that both electrodes are required to be subjected to a periodical renewal.

(4) Electric conductivity method

This is a method for measuring an electric conductivity of sulfuric acid. This method is simple at first thought. However, since the electric conductivity of sulfuric acid reaches its maximum value at its 30% concentration, the sulfuric acid concentration does not become a single-valued function of the electric conductivity (Issued by John Wiley & Sons Company, "Encyclopedia of Chemical Technology", second edition, vol. 19, page 446, 1969), so that the sulfuric acid concentration can not be calculated equivocally from the value of electric conductivity. For this reason, a complex data processing system is necessary which causes a high manufacturing cost.

On the other hand, a retainer type lead acid battery in which an electrolyte is impregnated in a glass mat, etc. has comes into wide use recently. The electrolyte has no flowability at all and the quantity of electrolyte is limited, so that no suspended liquid exists at all in this battery. Therefore, even the above method (1) can not be used.

SUMMARY OF THE INVENTION

An object of this invention is to provide a sulfuric acid concentration sensor enabling an easy measurement the concentration of sulfuric acid.

Another object of this invention is to provide a lead acid battery equipped with a sulfuric acid concentration sensor which is simple in its construction and inexpensive in its manufacturing cost.

This invention is made in due consideration of the above problems and with an intention to grasp a change in sulfuric acid concentration as an electric variation having a correlation to that change in a form of one-valued function.

The sulfuric acid concentration sensor of this invention includes a sensor body comprising a high molecular compound having a property to react with sulfuric acid and a property to change in electric conductivity as a one-valued function with a change in sulfuric acid concentration, so that an electric current flows through the sensor body impregnated in sulfuric acid solution to obtain the electric conductivity of the sensor body to thereby determine the sulfuric acid concentration.

The lead acid battery with a sulfuric acid concentration sensor of this invention is a lead acid battery equipped with a sulfuric acid concentration sensor, the sulfuric acid concentration sensor includes a sensor body comprising a high molecular compound having a property to react with sulfuric acid and a property to change in electric conductivity as a one-valued function with a change in sulfuric acid concentration, so that an electric current flows through the the sensor body to obtain the electric conductivity of sensor body so as to determine the sulfuric acid concentration, and the sensor body is installed under a state immersed in an electrolyte.

There is no special limitation as to the high molecular compound for use in the present invention so long as it has a property to react with sulfuric acid and a property to change in electric conductivity as a one-valued function with a change in sulfuric acid concentration. However, since the sulfuric acid solution itself has an electric conductivity to some extent, it is required for the high molecular compound to have a considerably large electric conductivity.

The high molecular compound may be formed from a compound shown by equation (I):

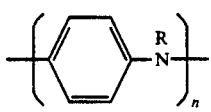
(I)

where R is a hydrogen group or a hydrocarbon group, and n is an integer over two, or a compound obtained by oxidizing that compound.

Polymers which are obtained by electrochemically oxidizing aromatic amine compounds shown by the following formulae (III) through (VII) or by oxidizing them chemically using an oxidizing agent, are preferably used for the above-mentioned high molecular compound. These polymers have a feature to include in their molecules nitrogen atoms which react with acids.

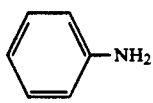
(III)

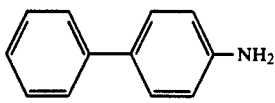
(IV)

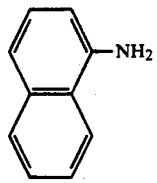
(V)

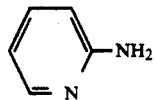
(VI)

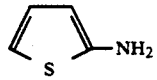
(VII)

The polyanilines obtained by oxidation of the aniline shown by the formulae (III) for example, it is well known that an emeraldin base type structure shown by the following equation (VIII) scarcely permits an electric current to pass, but an emeraldin acid type structure shown by the following equation (IX) has a large electric conductivity to an extent of 10 Scm$^{-1}$ (siemens per centimeter). (For instance, [1] F. L. Lu. et al., "Journal of American Chemical Society", vol. 108, page 8311, 1986; [2] Edited by Naoya Ogata, "Conductive Polymer", issued by Kodansha Scientific, page 75, 1990; [3] Written by Takakazu Yamamoto & Tsutomu Matsunaga, "Polymer Battery", issued by Kyoritsu Shuppan, page 34, 1990).

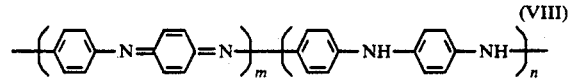
(VIII)

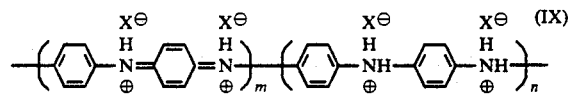
(IX)

(HX means an acid of hydrochloric acid, sulfuric acid etc.)

When the compound shown by the formula (IV) for example is oxidized to be polymerized, it forms a structure similar to the emeraldin base type structure shown by the following equation (X). When acid is added to it, it forms a structure similar to the emeraldin acid type structure shown by the following equation (XI) and can be effectively used for the sensor body. Naturally, a high molecular compound synthesized by a method other than the oxidation of aromatic amine may be effectively used for the sensor body.

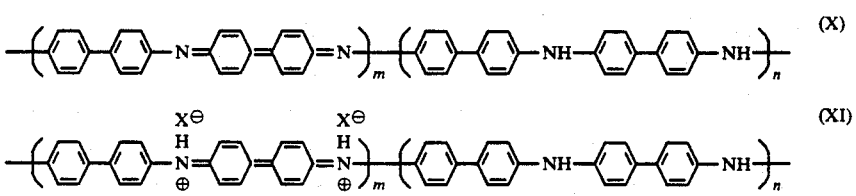
(X)

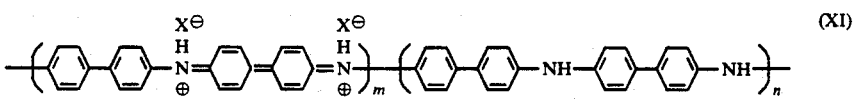
(XI)

The above-mentioned aromatic amine may be one comprising an aromatic ring having an alkyl group, an alkoxyl group, an amide group or a carboxyl group. Further, in addition to the foregoing compounds, the following high molecular compounds may be used in the present invention: i.e. π-conjugated polymers such as poly(pyrrole-2,5-diyl), poly(thiophene-2,5-diyl), and poly(arylene-vinylene), and their substitution derivative products which react with sulfuric acid and change the electric conductivity as a one-valued function according to the change of sulfuric acid concentration. A basic property of high molecular compound, a measuring range of sulfuric acid concentration and a measuring sensitivity, can be controlled in the above-mentioned high molecular compounds, when the kinds of aromatic rings and the substitution groups are properly selected.

According to an object such as control of an acid addition reaction of the above high molecular compounds or control of a stability of the above high molecular compounds in sulfuric acid solution, the above high molecular compounds may be coated with ceramic or other high molecular compound i.e. general purpose high molecular compound, (nylon, etc., for example), or may be mixed with them.

The type of current applied to the sensor body may be direct or alternate according to the object. The electric conductivity of the sensor body can be obtained by measuring a current value flowing through the sensor body, i.e., the above high molecular compound, or by measuring an electrical resistance value.

Since the sulfuric acid concentration varies within a range of 8 to 45% in a lead acid battery, it is significant to use the sulfuric acid concentration sensor of the present invention when the sulfuric acid concentration lies within this range.

The sulfuric acid concentration sensor of the present invention can be used not only for the measurement of sulfuric acid concentration in a sulfuric acid solution, but also for a measurement of sulfuric acid concentration in an organic solvent. As seen from the equation (VIII) in which the hydrochloric acid is added, the sulfuric acid concentration sensor of the present invention can be used for the concentration measurement not only of the sulfuric acid but also of other acids (such as hydrochloric acid, for example).

The electric conductivity of a high molecular compound for use in the present invention corresponds to the sulfuric acid concentration. Therefore, when the electric conductivity of the sensor body, i.e., high molecular compound, is obtained, the sulfuric acid concentration can be known.

The compound shown by the equation (I) or a compound obtained by oxidizing that compound or a polymer obtained by oxidizing an aromatic amine compound includes in its molecule nitrogen atoms which react with acid, so that a reaction with sulfuric acid certainly occurs and a change in the electric conductivity clearly takes place.

When the above high molecular compounds are used by coating them with other high molecular compound or by mixing them with other high molecular compound, the approach of the acid to the above high molecular compound is controlled so that the oxide addition reaction of the above high molecular compound and the stability of the above high molecular compound in sulfuric acid solution etc. are controlled.

Figure 1:
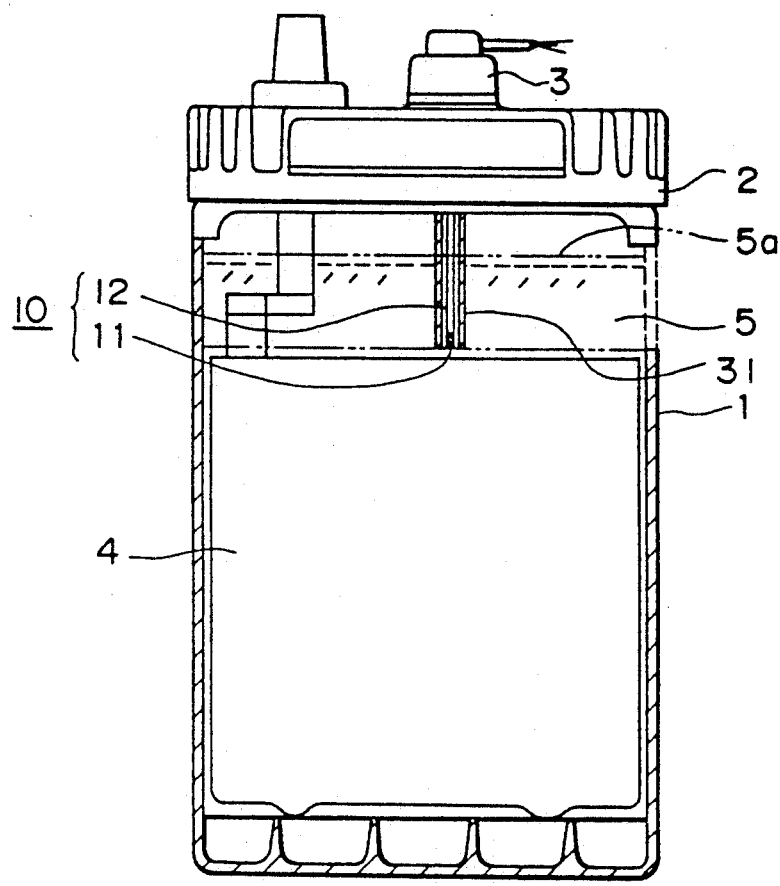
FIG. 1 is a vertical sectional view showing a lead acid battery equipped with a sulfuric acid concentration sensor of embodiment 2.

DESCRIPTION OF THE PREFERRED EMBODIMENTS (Embodiment 1

This embodiment relates to a sulfuric acid concentration sensor.

In the first place, polyaniline soluble in N-methylpyrrolidone was synthesized according to the method reported by Abe et al.(Preliminary Reports for Polymer Society, vol. 38, page 2139, 1989). Namely, aniline was oxidized and polymerized in an aqueous solution including sulfuric acid and hydrochloric acid by using ammonium peroxodisulfate so as to obtain a powdered polymer, and this powdered polymer was treated by aqueous ammonia so as to obtain emeraldin base type polyaniline.

In the next place, this polyaniline was dissolved in the N-methylpyrrolidone, the obtained solution was developed over the substrate, and a solvent was evaporated and removed under vacuum so as to obtain a black or dark purple film having a thickness of 89 microns. This film was cut into a rectangular shape of 7.2 mm × 10.5 mm and two shorter sides of the cut film were connected to platinum wires (0.25 mm dia.) respectively by using conductive carbon paste (made by Furuuchi Chemical Co., Ltd.), so that a sensor body was prepared.

This sensor body was immersed in an aqueous sulfuric acid a 19° C., an electrical resistance value was measured when a direct current voltage of 0.50 V was applied between the two platinum wires of the sensor body, and an electric conductivity of the film of the sensor body was obtained. Incidentally, the current generated by electrolysis of water in the aqueous sulfuric acid can almost be neglected under the applied voltage of 0.50 V. Further, the film, before being immersed in the aqueous sulfuric acid, had an electric conductivity of under $10^{-3}$ Scm$^{-1}$ so that it was substantially an insulator. As a result, the conductivity of the above film increased roughly monotonously as 2.4 Scm$^{-1}$, 3.1 Scm$^{-1}$, 3.1 Scm$^{-1}$, 3.2 Scm$^{-1}$, 3.3 Scm$^{-1}$, 3.4 Scm$^{-1}$, 3.4 Scm$^{-1}$, 3.5 Scm$^{-1}$ when the sulfuric acid concentration was increased as 8%, 15%, 20%, 25%, 30%, 35%, 40%, 45%. When the sensor body was immersed in an aqueous sulfuric acid of 8% after that, the conductivity of film returned to approximately original value (2.4 Scm$^{-1}$).

As described above, the electric conductivity of the film of the above sensor body correlates with the sulfuric acid concentration as a one-valued function so that it changes with a change in the sulfuric acid concentration. Consequently, the sulfuric acid concentration can be known when the electric conductivity of the film is obtained.

As seen from the foregoing description, according to the sulfuric acid concentration sensor of this embodiment, the sulfuric acid concentration can be known when the electric conductivity of sensor body is obtained. The electric conductivity of sensor body can be obtained easily, so that the sulfuric acid concentration can be measured easily by the sensor of this embodiment.

Especially, the compound shown by the equation (I) or the compound obtained by oxidizing that compound or the polymer obtained by oxidizing the aromatic amine compound includes in its molecule nitrogen atoms which react with acid, so that the reaction with sulfuric acid certainly occurs and the change in the electric conductivity takes place clearly. Therefore, when the above-mentioned polymer is used, the sulfuric acid concentration can be measured more correctly.

When the above high molecular compounds are used by coating them with other high molecular compound or by mixing them with other high molecular compounds, the oxide addition reaction of the above high molecular compound and the stability of the above high molecular compound in aqueous sulfuric acid etc. can be controlled. Accordingly, the sulfuric acid concentration can be measured under a stable state.

When the sensor of this embodiment is used under a sulfuric acid concentration ranging from 8 to 45%, a significant measurement can be carried out in order for measurement and control of charge/discharge of quantity of the lead acid battery.

(Embodiment 2

This embodiment relates to a lead acid battery equipped with a sulfuric acid concentration sensor.

Figure 2:
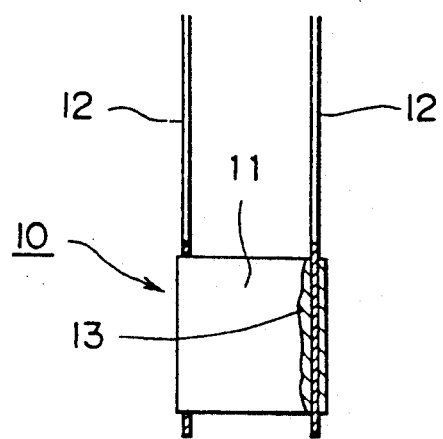
FIG. 2 is a view showing a sulfuric acid concentration sensor used in embodiment 2 and embodiment 3.

FIG. 1 is a vertical sectional view showing the lead acid battery equipped with a sulfuric acid concentration sensor of this embodiment. 1 denotes a container, 2 denotes a cover, 3 denotes a port plug closing an electrolyte filling port of the cover 2, 4 denotes a group of positive and negative plates housed in the container 1, 5 denotes an electrolyte, and 5a denotes an electrolyte level of the electrolyte 5. A cylindrical holder tube 31 extending perpendicularly downward is fit into the port plug 3, and a sulfuric acid concentration sensor 10 is installed in the holder tube 31. The holder tube 31 is so fit such that a large portion of it is immersed in the electrolyte 5. The sulfuric acid concentration sensor 10 includes a sensor body 11 and two platinum lead wires 12 as shown by FIG. 2 in an enlarged manner, so that an electric current flows to the sensor body 11 by a controller so as to measure the electric conductivity of the sensor body 11. The sensor body 11 is formed into a rectangular film-like shape and installed at a bottom portion of the holder tube 31. The platinum lead wires 12 are connected to both ends of the sensor body 11 by a conductive carbon paste 13, and extend upward in the holder tube 31 to be connected to said controller.

The sensor body 11 was prepared as described below. In the first place, aniline was oxidized and polymerized in an aqueous solution including sulfuric acid and hydrochloric acid by using ammonium peroxodisulfate so as to obtain a powdered polymer, and this powdered polymer was treated by aqueous ammonia so as to obtain emeraldin base type polyaniline. In the next place, this polyaniline was dissolved in N-methylpyrrolidone, the obtained solution was developed over the substrate, and a solvent was evaporated and removed under vacuum so as to obtain a film having a thickness of 90 microns. This film was cut to a rectangular shape of 7.2 mm × 10.5 mm so that the sensor body 11 was prepared.

Figure 3:
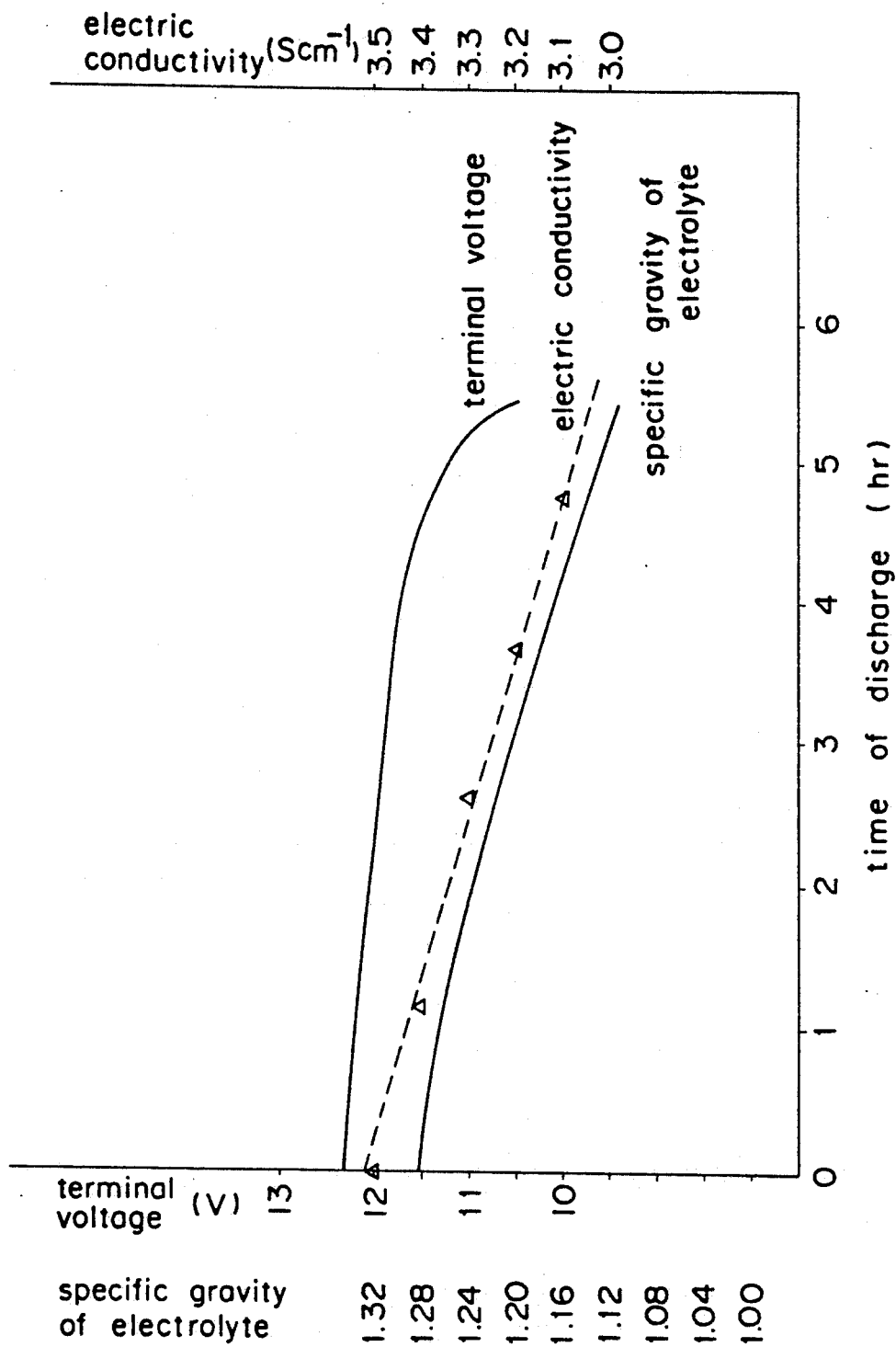
FIG. 3 is a diagram showing changes in a terminal voltage, a specific gravity of electrolyte and an electric conductivity when the battery of embodiment 2 is discharged at a constant current.

The lead acid battery having the above structure has the characteristics of 12 V and 33 Ah, incorporates a sulfuric acid solution having a specific gravity of 1.28 as the electrolyte 5, and is in a fully charged state. In this lead acid battery, a direct current voltage of 0.5 V including no possibility of electrolysis of water was applied between the two platinum lead wires 12, and a measured electric conductivity was proved to be 3.5 Scm$^{-1}$. FIG. 3 shows changes in the terminal voltage (discharge voltage), the specific gravity of electrolyte, and the electric conductivity of the sensor body 11, when the lead acid battery is discharged at a specified current of 4.8 A.

As seen from FIG. 3, the change in electric conductivity is approximately in proportion to the change in specific gravity of electrolyte i.e. the sulfuric acid concentration, so that the obtained electric conductivity of the sensor body 11 results in knowledge of the sulfuric acid concentration. The changes in electric conductivity and specific gravity of electrolyte correlate with the change in terminal voltage in the manner of a one-valued function. Consequently, the obtained electric conductivity of the sensor body 11 results in knowledge of the terminal voltage, i.e., the charge/discharge quantity.

The sulfuric acid concentration sensor 10 for use in the lead acid battery as constructed above is composed merely of the sensor body 11 and the platinum lead wires 12 etc., so that it is simple in its construction and inexpensive in its manufacturing cost. Moreover, it is sufficient to flow a current through the sensor body 11 so as to obtain the electric conductivity of the sensor body 11, so that this sensor is easy in its use.

As described above, the lead acid battery of this embodiment is equipped with the sulfuric acid concentration sensor 10 which enables determination of the specific gravity of electrolyte, i.e., the sulfuric acid concentration, by obtaining the electric conductivity, so that the charge/discharge quantity can be known easily. Further, the sulfuric acid concentration sensor 10 is composed merely of the sensor body 11 and the platinum lead wires 12, etc., so that it is simple in its construction and inexpensive in its manufacturing cost.

When the compound specially shown by the equation (I) or the compound obtained by oxidizing that compound or the polymer obtained by oxidizing the aromatic amine compound is used for the high molecular compound composing the sensor body 11, it includes in its molecule nitrogen atoms which react with acid so that the reaction with sulfuric acid certainly occurs and the change in the electric conductivity clearly takes place. Therefore, the sulfuric acid concentration i.e. the charge/discharge quantity can be known more correctly.

Further, when the above high molecular compounds are used by coating them with other high molecular compounds or by mixing them with other high molecular compounds, the oxide addition reaction of the above high molecular compound and the stability of the above high molecular compound in sulfuric acid solution etc. can be controlled. Accordingly, the sulfuric acid concentration can be measured under a stable state.

(Embodiment 3

This embodiment also relates to a lead acid battery equipped with a sulfuric acid concentration sensor.

Figure 4:
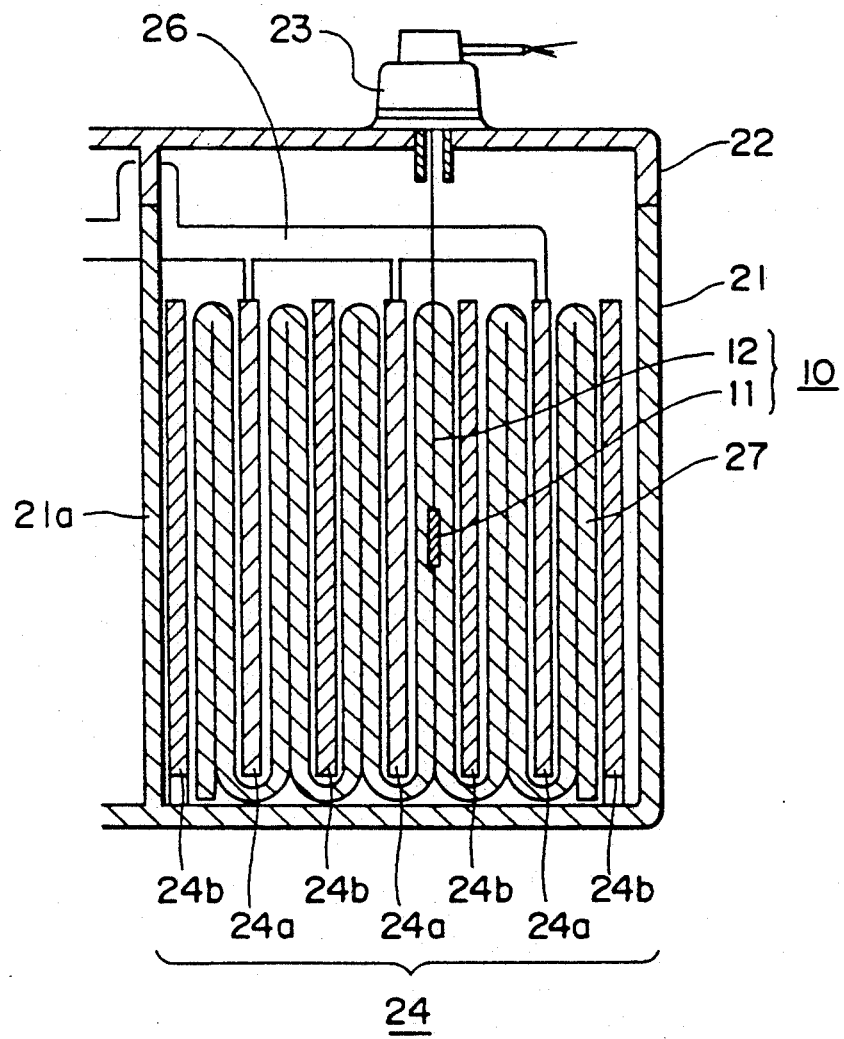
FIG. 4 is a vertical sectional view showing a lead acid battery equipped with a sulfuric acid concentration sensor of embodiment 3.

FIG. 4 is the vertical sectional view showing the lead acid battery equipped with the sulfuric acid concentration sensor of this embodiment. 21 denotes a container, 21a denotes a partition which partitions the container 21 into plural chambers, 22 denotes a cover, 23 denotes a port plug closing an electrolyte filling port of the cover 22, and 24 denotes a group of positive and negative plates housed in the container 21, 24a denoting a positive plate, and 24b denotes a negative plate. 26 denoting a strap for connecting the positive plate 24a to an outside terminal. A film 27 comprising a glass mat is installed between the adjoining plates 24a and 24b. The film 27 is bent into a twofold shape at its upper portion in between the adjoining plates 24a and 24b. The film 27 is impregnated with an electrolyte, so that a fluidity of the electrolyte is thereby restricted and a quantity of the electrolyte becomes very small, so as to provide a state where no suspended liquid exists at all apparently. That is, the battery of this embodiment is of a retainer type.

In the battery as constructed above, the sulfuric acid concentration sensor 10 is installed such that is as sandwiched between the twofold portions of the film 27. Namely, the sensor body 11 is held between the films 27 in parallel to the plates 24a and 24b, and the platinum lead wires 12 penetrate the upper twofold portion of the film 27 to be connected to the port plug 23. Since the thickness of the sensor body 11 is only 0.2 mm, its thickness is absorbed by the elasticity of the film 27, an existence state of the sensor body which makes no apparent difference at all relative to a no-existence state thereof. A sulfuric acid concentration sensor 10 is installed in each chamber partitioned by the partition 21a. Incidentally, the sensor body 11 is the same as that of embodiment 2.

In the lead acid the battery having the above structure, battery characteristics are 12 V and 33 Ah, the film 27 is impregnated with sulfuric acid solution having a specific gravity of 1.28, and the battery is in a fully charged state. In this lead acid battery, a direct current voltage of 0.5 V including no possibility of electrolysis of water was applied between the two platinum lead wires 12, and a measured electric conductivity was proved to be 3.5 Scm$^{-1}$. The battery was further discharged at 4.8 A for 5 hours, and a measured electric conductivity was proved to be 3.0 Scm$^{-1}$.

This embodiment also has the same function and effect as the embodiment 2. Namely, since the sensor body 11 is in contact with the electrolyte of the film 27, the obtained electric conductivity of the sensor body 11 results in knowledge of the charge/discharge quantity in the same manner as the embodiment 2. Moreover, the sensor body is simple in its construction, so that it is inexpensive in manufacturing cost and easy to use.

Since the sensor body 11 is held between the films 27, it is preferable to use a material therefor through which the electrolyte, especially sulfuric acid ions, are permeable. A sheet including fine pores such as a porous film or a woven cloth is appropriate.

As described above, the sulfuric acid concentration sensor 10 can be used also for a battery incorporating an electrolyte in a gelled state or a retainer type battery, so that the charge/discharge quantity can be known easily in a wide range of batteries.

What is claimed is:

1. A sulfuric acid concentration sensor including a sensor body comprising a high molecular compound having a property to react with sulfuric acid and a property to change in electric conductivity as a one-valued function with a change in sulfuric acid concentration, in which an electric current can be passed through the sensor body while in contact with a sulfuric acid solution to obtain the electric conductivity of the sensor body so as to determine the sulfuric acid concentration of the sulfuric acid solution.

2. A sulfuric acid concentration sensor as set forth in claim 1, in which the high molecular compound is a compound shown by an equation (I) or a compound obtained by oxidizing that compound:

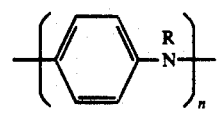

where R is a hydrogen group or a hydrocarbon group, and n is an integer more than two.

3. A sulfuric acid concentration sensor as set forth in claim 1, in which the high molecular compound is a polymer obtained by oxidizing an polymerizing an aromatic amine compound.

4. A sulfuric acid concentration sensor as set forth in claim 1, in which the high molecular compound is coated with another high molecular compound or mixed with another high molecular compound.

5. A sulfuric acid concentration sensor as set forth in claim 1, in which a sulfuric acid concentration in the sulfuric acid solution is within a range of 8 to 45 wt. %.

6. A lead acid battery equipped with a sulfuric acid concentration sensor, the sulfuric acid concentration sensor including a sensor body comprising a high molecular compound having a property to react with sulfuric acid and a property to change an electric conductivity as a one-valued function with a change in sulfuric acid concentration, in which an electric current can be passed through the sensor body to obtain the electric conductivity of sensor body so as to determine sulfuric acid concentration, and the sensor body being installed immersed in an electrolyte of the battery.

7. A lead acid battery equipped with a sulfuric acid concentration sensor as set forth in claim 6, in which the electrolyte is in a gelled state.

8. A lead acid battery equipped with a sulfuric acid concentration sensor as set forth in claim 6, in which the electrolyte is held by separators, the sensor body is formed into a film-like shape, and the sulfuric acid concentration sensor is installed such that the sensor body is sandwiched between the separators.

9. A lead acid battery equipped with a sulfuric acid concentration sensor as set forth in claim 6, in which the high molecular compound is a compound shown by an equation (I) or a compound obtained by oxidizing that compound:

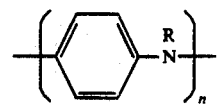

where R is a hydrogen group or a hydrocarbon group, and n is an integer of more than two.

10. A lead acid battery equipped with a sulfuric acid concentration sensor as set forth in claim 6, in which the high molecular compound is a polymer obtained by oxidizing and polymerizing an aromatic amine compound.

11. A lead acid battery equipped with a sulfuric acid concentration sensor as set forth in claim 6, in which the high molecular compound is coated with another high molecular compound or mixed with another high molecular compound.

* * * * *